(12) United States Patent
Imperiali et al.

(10) Patent No.: US 10,799,603 B2
(45) Date of Patent: Oct. 13, 2020

(54) KINASE AND/OR PHOSPHATASE SENSING VIA HYDROXYQUINOLINE-SENSITIZED CHELATES

(71) Applicants: Massachusetts Institute of Technology, Cambridge, MA (US); Centre National de la recherche scientifique, Paris (FR); ENSCM, Montpellier (FR); UNIVERSITE DE MONTPELLIER, Montpellier (FR)

(72) Inventors: Barbara Imperiali, Cambridge, MA (US); Juan Antonio González Vera, Granada (ES)

(73) Assignees: Massachusetts Institute of Technology, Cambridge, MA (US); Centre National de la Recherche Scientifique, Paris (FR); ENSCM, Montpellier (FR); UNIVERSITE DE MONTPELLIER, Montpellier (FR)

( * ) Notice: Subject to any disclaimer, the term of this patent is extended or adjusted under 35 U.S.C. 154(b) by 0 days.

(21) Appl. No.: 16/299,976

(22) Filed: Mar. 12, 2019

(65) Prior Publication Data
US 2019/0275172 A1 Sep. 12, 2019

Related U.S. Application Data

(60) Provisional application No. 62/641,587, filed on Mar. 12, 2018.

(51) Int. Cl.
| | | |
|---|---|---|
| *A61K 49/00* | (2006.01) | |
| *A61K 31/472* | (2006.01) | |
| *C07K 7/08* | (2006.01) | |
| *A61K 51/08* | (2006.01) | |
| *G01N 33/58* | (2006.01) | |
| *G01N 33/52* | (2006.01) | |
| *C12Q 1/48* | (2006.01) | |
| *G01N 33/542* | (2006.01) | |

(52) U.S. Cl.
CPC ........ *A61K 49/0002* (2013.01); *A61K 31/472* (2013.01); *A61K 49/0056* (2013.01); *A61K 51/088* (2013.01); *C07K 7/08* (2013.01); *C12Q 1/485* (2013.01); *G01N 33/52* (2013.01); *G01N 33/542* (2013.01); *G01N 33/582* (2013.01)

(58) Field of Classification Search
CPC .......................... A61K 49/0002; A61K 31/472
See application file for complete search history.

(56) References Cited

U.S. PATENT DOCUMENTS

| | | |
|---|---|---|
| 6,906,194 B2 | 6/2005 | Imperiali et al. |
| 7,262,282 B2 | 8/2007 | Imperiali et al. |
| 7,442,529 B2 | 10/2008 | Imperiali et al. |
| 7,892,775 B2 | 2/2011 | Imperiali et al. |
| 7,964,729 B2 | 6/2011 | Imperiali et al. |
| 8,409,820 B2 | 4/2013 | Imperiali et al. |
| 8,440,835 B2 | 5/2013 | Imperiali et al. |
| 8,586,570 B2 | 11/2013 | Imperiali et al. |
| 2005/0080243 A1 | 4/2005 | Imperiali |
| 2008/0206885 A1 | 8/2008 | Imperiali et al. |
| 2009/0082577 A1 | 3/2009 | Imperiali et al. |

FOREIGN PATENT DOCUMENTS

| | | |
|---|---|---|
| WO | WO 2005/037859 A2 | 4/2005 |
| WO | WO 2008/082715 A2 | 7/2008 |
| WO | WO 2011/025546 A1 | 3/2011 |

OTHER PUBLICATIONS

PCT/US2019/021917, Jul. 11, 2019, International Search Report and Written Opinion.
International Search Report and Written Opinion for Application No. PCT/US2019/021917 dated Jul. 11, 2019.
Beck et al., Interrogating Endogenous Protein Phosphatase Activity with Rationally Designed Chemosensors. ACS Chem Biol. Jan. 15, 2016;11(1):284-90. doi: 10.1021/acschembio.5b00506. Epub Dec. 3, 2015.
Gonzalez-Vera et al., Fluorescent Reporters and Biosensors for Probing the Dynamic Behavior of Protein Kinases. Proteomes. Nov. 4, 2015;3(4):369-410. doi: 10.3390/proteomes3040369. Review.
Tremblay et al., A luminescent sensor for tyrosine phosphorylation. Org Lett. Jan. 3, 2008;10(1):5-8. Epub Dec. 11, 2007.
Tremblay et al., Phosphorylation state-responsive lanthanide peptide conjugates: a luminescence switch based on reversible complex reorganization. Org Lett. Jun. 22, 2006;8(13):2723-6.

*Primary Examiner* — Noble E Jarrell
(74) *Attorney, Agent, or Firm* — Wolf, Greenfield & Sacks, P.C.

(57) ABSTRACT

The present invention generally relates to assays of enzymes responsible for phosphoregulation including kinases (such as protein kinases, which mediate protein and peptide phosphorylation) and phosphatases (such as protein phosphatases, which mediate protein and peptide dephosphorylation). Certain aspects of the invention use lanthanide ions such as europium ions that exhibit chelation-enhanced luminescence. Phosphorylation of a peptide by a kinase may cause a complex to form between the lanthanide ion, the phosphate group, and a reporter group such as a hydroxyquinoline, which results in luminescence when in the complexed state. Thus, in certain embodiments, determination of luminescence may be indicative of kinase activity. Certain embodiments also include the use of substrates for detection of phosphatase activity, where dephosphorylation results in a loss of signal assay. Other aspects are generally related to techniques for making and using such peptides or complexes, kits involving such peptides or complexes, and the like.

21 Claims, 5 Drawing Sheets

Specification includes a Sequence Listing.

Kinetic Standard
Method-Global Fit

Endpoint Red Shift
Assay- No Stop Solution

Endpoint Red Shift
+ Stop Solution

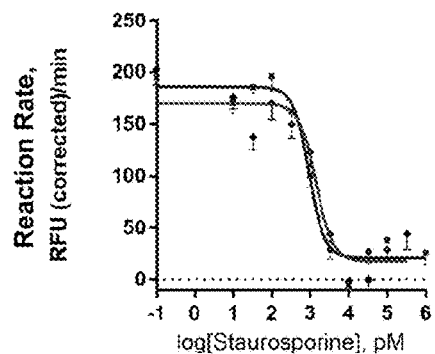
FIG. 8A
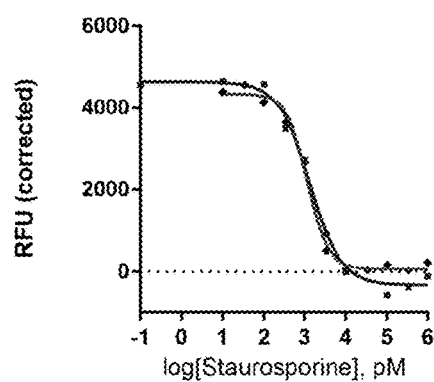
FIG. 8B
FIG. 9A
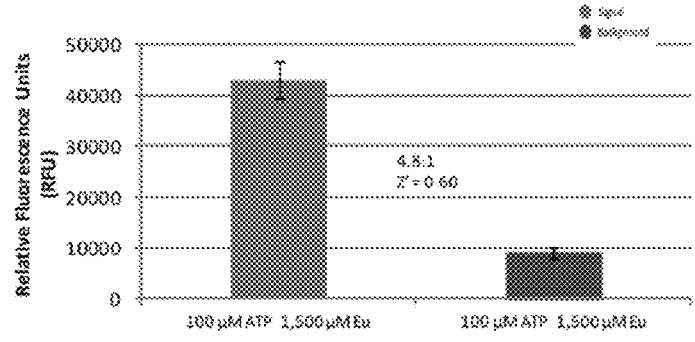
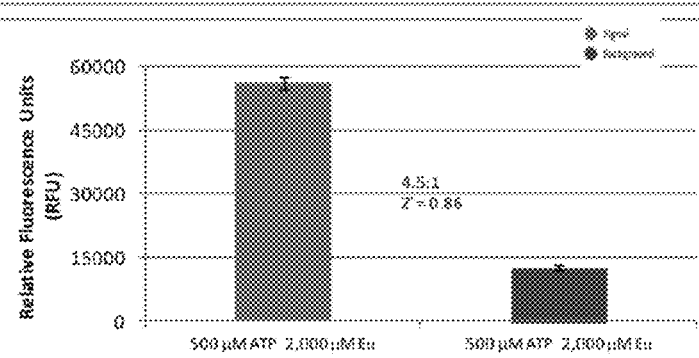
FIG. 9B

KINASE AND/OR PHOSPHATASE SENSING VIA HYDROXYQUINOLINE-SENSITIZED CHELATES

RELATED APPLICATIONS

This application claims the benefit of U.S. Provisional Patent Application Ser. No. 62/641,587, filed Mar. 12, 2018, entitled "Kinase and/or Phosphatase Sensing Via Hydroxyquinoline-Sensitized Chelates," by Imperiali, et al., incorporated herein by reference in its entirety.

GOVERNMENT FUNDING

This invention was made with Government support under Grant No. GM064346 awarded by the National Institutes of Health (NIH). The Government has certain rights in the invention.

FIELD

The present invention generally relates to assays of enzymes responsible for phosphoregulation including kinases (such as protein kinases, which mediate protein and peptide phosphorylation) and phosphatases (such as protein phosphatases, which mediate protein and peptide dephosphorylation). For clarity, the descriptions provided generally focus on protein kinases to illustrate certain the embodiments of this invention, but it should be understood that in other embodiments, phosphatases may be used.

BACKGROUND

Protein kinases are involved in aspects of regulation within cells. Protein kinases generally act by adding phosphoryl groups (phosphorylation) to certain amino acid residues such as serine, threonine, or tyrosine. Phosphorylation often results in a functional change of the target protein (substrate) by changing enzyme activity, cellular location, or association with other proteins. Protein kinases are found in a wide variety of organisms, including animals, plants, and bacteria. Detection of phosphorylation events within proteins is often done with fluorescence, but can be difficult due to background fluorescence, e.g., in the presence of large libraries of small molecule organic compounds. Accordingly, improvements are needed.

SUMMARY

The present invention generally relates to assays of kinases such as protein kinases, which mediate protein and peptide phosphorylation. The subject matter of the present invention involves, in some cases, interrelated products, alternative solutions to a particular problem, and/or a plurality of different uses of one or more systems and/or articles.

In one aspect, the present invention is generally directed to a composition. In one set of embodiments, the composition comprises a peptide having a first portion comprising a structure:

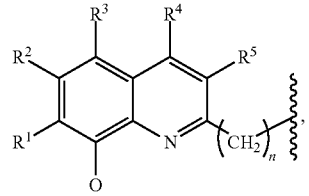

where each of $R^1$, $R^2$, $R^3$, $R^4$, and $R^5$ independently is hydrogen or $-SO_2X$ such that at least one of $R^1$, $R^2$, $R^3$, $R^4$, and $R^5$ is $-SO_2X$, where X is $-OR'$ or $-NR'R''$, R' and R'' each independently being hydrogen or an alkyl, and n is 0 or a positive integer, and a second portion comprising a phosphate group, where the N and/or the O of the first portion, and the phosphate group of the second portion, are coordinated via a lanthanide ion.

The composition, in another set of embodiments, comprises a solution comprising dissolved lanthanide ions and a peptide comprising a portion having a structure:

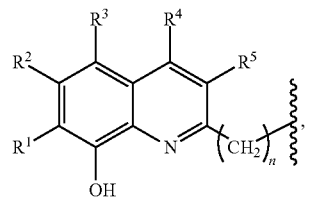

where each of $R^1$, $R^2$, $R^3$, $R^4$, and $R^5$ independently is hydrogen or $-SO_2X$ such that at least one of $R^1$, $R^2$, $R^3$, $R^4$, and $R^5$ is $-SO_2X$, where X is $-OR'$ or $-NR'R''$, R' and R'' each independently being hydrogen or an alkyl, n is 0 or a positive integer, and the wavy line indicates covalent attachment to the peptide.

In another aspect, the present invention is generally directed to a method. In one set of embodiments, the method includes noncovalently binding a lanthanide ion to a peptide comprising a first portion, and a second portion comprising a phosphate group, where the first portion has a structure:

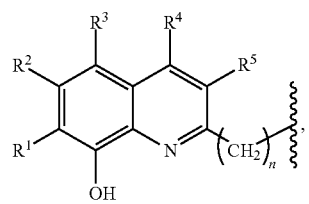

where each of $R^1$, $R^2$, $R^3$, $R^4$, and $R^5$ independently is hydrogen or $-SO_2X$ such that at least one of $R^1$, $R^2$, $R^3$, $R^4$, and $R^5$ is $-SO_2X$, where X is $-OR'$ or $-NR'R''$, R' and R'' each independently being hydrogen or an alkyl, n is 0 or a positive integer, and the wavy line indicates covalent attachment to the peptide; and determining luminescence of the structure to determine binding of the lanthanide ion to the first and second portions of the peptide.

The method, in accordance with another set of embodiments, includes exposing a kinase to a peptide and magnesium ions, where after phosphorylation of the peptide by the kinase, the magnesium ions non-covalently bind to the peptide to form a complex; exposing the complex to europium ions; and determining luminescence of the complex to determine phosphorylation of the peptide by the kinase.

In yet another set of embodiments, the method comprises exposing a kinase to a peptide comprising a first portion, and a second portion comprising a phosphate group, where the first portion has a structure:

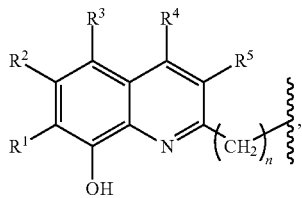

where each of $R^1$, $R^2$, $R^3$, $R^4$, and $R^5$ independently is hydrogen or —$SO_2X$ such that at least one of $R^1$, $R^2$, $R^3$, $R^4$, and $R^5$ is —$SO_2X$, where X is —OR' or —NR'R", R' and R" each independently being hydrogen or an alkyl, n is 0 or a positive integer, and the wavy line indicates covalent attachment to the peptide; and determining phosphorylation of the peptide by determining luminescence of the structure at 616+/−5 nm.

In still another set of embodiments, the method includes exposing a solution suspected of containing a phosphatase to a phosphorylated peptide and magnesium ions; exposing the complex to europium ions; and determining luminescence of the complex to determine dephosphorylation of the peptide by the phosphatase.

The method, in yet another set of embodiments, includes exposing a phosphatase to a peptide comprising a first portion, and a second portion comprising a phosphate group, where the first portion has a structure:

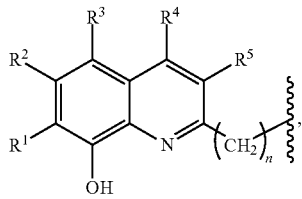

where each of $R^1$, $R^2$, $R^3$, $R^4$, and $R^5$ independently is hydrogen or —$SO_2X$ such that at least one of $R^1$, $R^2$, $R^3$, $R^4$, and $R^5$ is —$SO_2X$, where X is —OR' or —NR'R", R' and R" each independently being hydrogen or an alkyl, n is 0 or a positive integer, and the wavy line indicates covalent attachment to the peptide; and determining dephosphorylation of the peptide by determining luminescence of the structure at 616+/−5 nm.

In another aspect, the present invention encompasses methods of making one or more of the embodiments described herein. In still another aspect, the present invention encompasses methods of using one or more of the embodiments described herein.

Other advantages and novel features of the present invention will become apparent from the following detailed description of various non-limiting embodiments of the invention when considered in conjunction with the accompanying figures.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures:

FIGS. 8A-8B illustrate the application of a hydroxyquinoline-sensitized Eu chelate to determine the $IC_{50}$ of staurosporine IC50 using a CaMK2δ kinase, in another embodiment of the invention; and FIGS. 9A-9B illustrate the application of a hydroxyquinoline-sensitized Eu chelate to assess activity of ASK1 kinase at low and high ATP concentrations.

BRIEF DESCRIPTION OF SEQUENCE VARIANTS

SEQ ID NO: 1 is LVEPLTPCGEA, a non-limiting example of a substrate for certain proline-directed serine/threonine kinases;

SEQ ID NO: 2 is Sox-OH, having the sequence LVEPLTPC(Sox)GEA, where T is unphosphorylated, and "Sox" has the following structure, where the wavy line indicates attachment to the S of the cysteine:

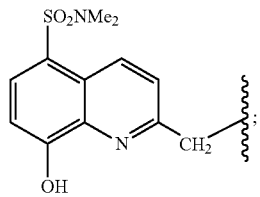

SEQ ID NO: 3 is Sox-P, having the sequence LVEPLT*PC(Sox)GEA, where T is phosphorylated (shown as T*), and "Sox" has the following structure, where the wavy line indicates attachment to the S of the cysteine:

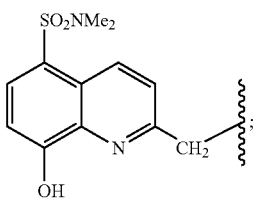

SEQ ID NO: 4 is Ac-EEPIYVC(Sox)FG, where "Sox" has the following structure, where the wavy line indicates attachment to the S of the cysteine:

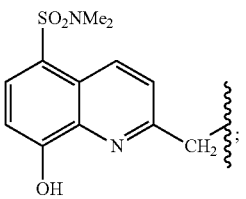

SEQ ID NO: 5 is Thr-Val-C(Sox)-Ala-Leu, where "Sox" has the following structure, where the wavy line indicates attachment to the S of the cysteine:

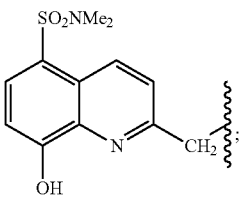

SEQ ID NO: 6 is Tyr-Arg-C(Sox)-Pro-Ser, where "Sox" has the following structure, where the wavy line indicates attachment to the S of the cysteine:

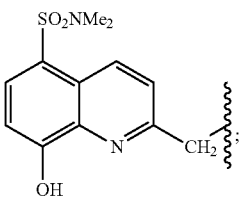

and

SEQ ID NO: 7 is Ac—C(Sox)-Gly-Thr-Phe, where "Sox" has the following structure, where the wavy line indicates attachment to the S of the cysteine:

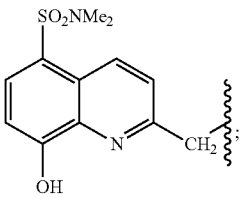

DETAILED DESCRIPTION

The present invention generally relates to assays of enzymes responsible for phosphoregulation including kinases (such as protein kinases, which mediate protein and peptide phosphorylation) and phosphatases (such as protein phosphatases, which mediate protein and peptide dephosphorylation). Certain aspects of the invention use lanthanide ions such as europium ions that exhibit chelation-enhanced luminescence. Phosphorylation of a peptide by a kinase may cause a complex to form between the lanthanide ion, the phosphate group, and a reporter group such as a hydroxyquinoline, which results in luminescence when in the complexed state. Thus, in certain embodiments, determination of luminescence may be indicative of kinase activity. Certain embodiments also include the use of substrates for detection of phosphatase activity, where dephosphorylation results in a loss of signal assay. Other aspects are generally related to techniques for making and using such peptides or complexes, kits involving such peptides or complexes, and the like.

Figure 1A:
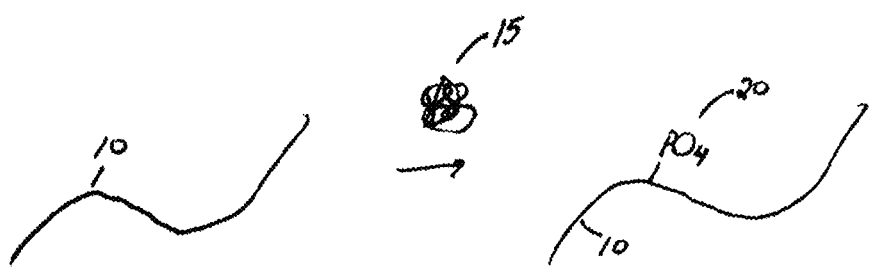
FIGS. 1A-1C are schematic diagrams illustrating certain structures in accordance with some embodiments of the invention.

One aspect of the invention is now described with respect to FIG. 1A. In this figure, a peptide 10 is exposed to a kinase, such as protein kinase 15, which transfers a phosphoryl group 20 to the peptide, e.g., on certain amino acid residues such as serine, threonine, or tyrosine. In certain embodiments, however, determination of the phosphorylation event, qualitatively and/or quantitatively, may be desired. In addition, it should be understood that in other embodiments, a phosphatase may be used.

Figure 1B:
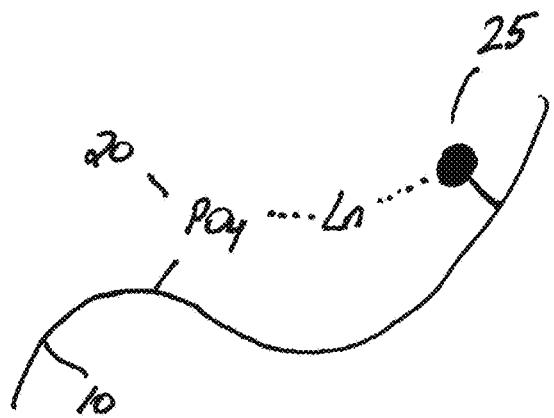

In some cases, such as is shown in FIG. 1B, this may be accomplished by using a group such as a hydroxyquinoline and ions that can non-covalently coordinate with the reporter group and the phosphate. Thus, in this figure, a lanthanide (III) [Ln(III)] ion is complexed to both phosphate 20 and reporter group 25 on peptide 10.

Figure 1C:
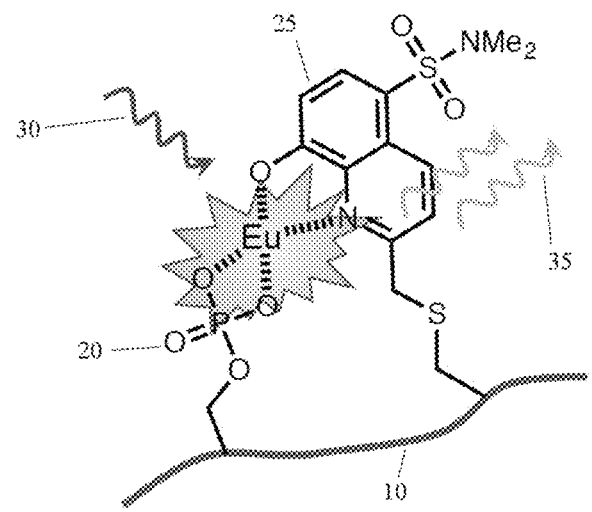

One non-limiting example of such a compound is illustrated in FIG. 1C, with europium (III) [Eu(III)] as the lanthanide ion. In this figure, peptide 10 includes both a phosphate group 20 and a hydroxy-quinoline group 25. Eu(III) is non-covalently coordinated to both of these groups. Upon application of incident light 30 of a suitable wavelength, the complex is able to luminesce, producing emissive light 35 that can be determined in some fashion, e.g., which can be used to determine that the peptide has been phosphorylated or not (for example, by a kinase or a phosphatase). However, if no phosphate group 20 is present, then the complex is not able to form (or forms poorly), and emissive light 35 is not produced (or is produced, but at a much weaker signal). Accordingly, for instance, the presence of a kinase or a phosphatase able to phosphorylate the peptide can be determined, e.g., qualitatively and/or quantitatively.

It should be understood, however, that other emissive groups besides the one shown in FIG. 1C are also possible in other embodiments of the invention; similarly, lanthanides other than europium may be used in some cases. Also, such systems are not limited to only the detection of kinases such as protein kinases. For instance, in one embodiment, such a system could be used to determine whether a phosphate is present on a structure or not. In another embodiment, a phosphopeptide could be used to measure the activity of a protein phosphatase. In yet another embodiment, the system may be used to determine a phosphatase.

In some aspects of the invention, a common structure, such as a peptide or a protein, may have a first portion having a reporter group, and a second portion able to phosphorylated, such that if the second portion is phosphorylated (i.e., modified by the covalent addition of a phosphate group), upon noncovalent binding or chelation to a suitable ion (such as a lanthanide ion), a complex forms between the ion, the phosphate, and the reporter group. In contrast, if the second portion is not phosphorylated, then the complex is not able to form, or is not able to form properly. As non-limiting examples, the second portion may not be phosphorylated because no kinase is present, or the phosphate group is subsequently removed, or because the second portion is not able to be phosphorylated due to some reason, for example, due to mutation, an interfering chemical reaction, steric hindrance, or the like.

In some cases, the complex, when formed, can be determined by a luminescence signal. For example, if the complex is present, then incident light of a suitable wavelength may cause the complex to luminesce and produce emissive light that can be determined, e.g., qualitatively or quantitatively. In some embodiments, the complex may comprise a hydroxyquinoline group.

For example, the complex may have a structure:

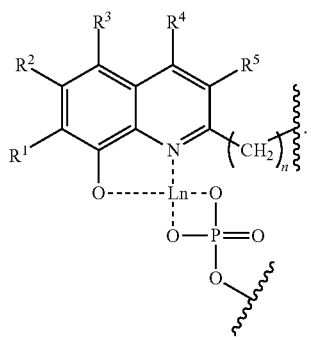

In this structure, the phosphate is at the bottom and the reporter group (in this example, a hydroxyquinoline group) is at the top, both chelated to a lanthanide ion (Ln). The wavy lines indicate attachment, e.g., to a common structure such as a peptide or protein. In some embodiments, other common structures may be present. For example, the common structure may be a nucleic acid, a glycan, phospholipid, or a synthetic polymer.

In addition, it should be understood that Ln may also complex to other ligands, such as $H_2O$ (not illustrated here for purposes of clarity). For example, the Ln may form complexes that coordinate to 6, 7, 8, 9, or more ligands in all. Thus, for example, the Ln above may also be coordinated to 2, 3, 4, 5, or more $H_2O$ molecules, e.g., in addition to the bonds that are shown.

If the common structure is a peptide or protein, there may be any suitable number of amino acid residues between the two attachment points. For example, there may be 1, 2, 3, 4, 5, 6, 7, 8, 9, or 10 or more amino acid residues between the two attachment points, and either one may be closer to the N-terminus or the C-terminus. The peptide or protein itself may have any suitable number of amino acid residues. For example, the peptide or protein may have at least 5, at least 10, at least 15, at least 20, at least 25, at least 30, at least 40, at least 50, at least 75, or at least 100 amino acid residues. In some cases, the peptide or protein may have less than 75, less than 50, less than 25, less than 20, less than 15, or less than 10 amino acid residues. The amino acids may include naturally-occurring and/or synthetic amino acids.

As mentioned, a second portion of the common structure may include a moiety able to be phosphorylated, e.g., to introduce the phosphate group shown above. For instance, the second portion may include serine, threonine, or tyrosine, wherein the phosphoryl group is transferred to the oxygen in the amino acid side chain. In some cases, the second portion may include a naturally-occurring or synthetic amino acid residue that includes a hydroxyl group in the side chain. In addition, in certain embodiments, the second portion can include histidine, lysine, or arginine (which may be phosphorylated through phosphoramidate bonds), or aspartic acid or glutamic acid (which may be phosphorylated through mixed anhydride linkages). Thus, as a non-limiting example, a phosphorylatable amino acid such as serine, threonine, or tyrosine may have a free —OH group such as that shown in FIG. 2 and defined as Sox-OH in SEQ ID NO: 2; upon phosphorylation (e.g., by a kinase), the OH may be converted to a —$OPO_3^=$ phosphate group (i.e., as —$OPO_3^=$ as shown in this figure and defined as Sox-P in SEQ ID NO: 3).

The lanthanide ion may be any suitable lanthanide ion. In one embodiment, the lanthanide is europium. In other embodiments, the lanthanide may be samarium, terbium, or dysprosium. In most cases, the lanthanide within the complex will be in the +3 state, but may be in the +2 state.

The first portion of the complex may be a reporter group such as a hydroxyquinoline, in certain embodiments. In some cases, the quinoline may have a structure:

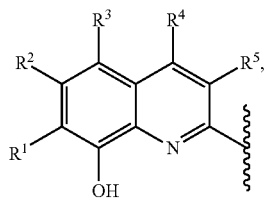

where the wavy line indicates covalent attachment to a peptide or other common structure, e.g., as discussed below. In some cases, chelation, coordination or non-covalent binding of a lanthanide ion may occur with the oxygen and the nitrogen atoms. In addition, in some cases, each of $R^1$, $R^2$, $R^3$, $R^4$, and $R^5$ independently can be hydrogen or a —$SO_2X$ moiety such that one, two, or more, of $R^1$, $R^2$, $R^3$, $R^4$, and $R^5$ is a —$SO_2X$ moiety. X in such structures may, in certain cases, be —OR' or —NR'R", where R' and R" each independently is hydrogen or an alkyl. R' and R" may be the same or different from each other. The alkyl group may have 1, 2, 3, 4, 5, 6, 7, 8, or more carbon atoms, may be unsubstituted or substituted, cyclic or linear, and may be saturated or unsaturated. Non-limiting examples of alkyl groups include methyl, ethyl, propyl, isopropyl, n-butyl, t-butyl, isobutyl, sec-butyl, cyclohexyl, cyclopentyl, (cyclohexyl)methyl, cyclopropylmethyl, etc. Non-limiting examples of substituted alkyls include haloalkyls, thioalkyls, aminoalkyls, chloromethyl, fluoromethyl, trifluoromethyl, 1-chloroethyl, 2-chloroethyl, etc.

As a non-limiting example, in one set of embodiments, the hydroxyquinoline has a structure:

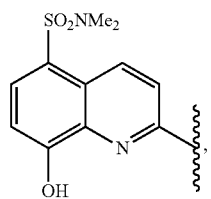

i.e., where $R^1$, $R^2$, $R^4$ and $R^5$ are each hydrogen, and $R^3$ is —$SO_2X$, where X is NR'R" and each of R' and R" is independently methyl. In other embodiments, the hydroxyquinoline may have structures such as:

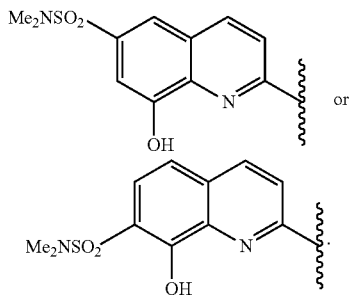

In addition, as previously mentioned, two or more —$SO_2X$ groups may be present, e.g., as substituents on the quinoline or other reporter group in some cases.

As mentioned, the reporter group may be covalently attached to a common structure, such as a peptide or a protein, at the location indicated by the wavy line. In some embodiments, there may also be one or more linkers within the reporter group, such as one or more —$CH_2$— groups, to facilitate attachment, i.e., as in the structure:

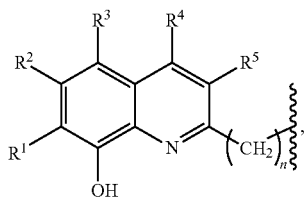

where n is 0 or a positive integer (e.g., 1, 2, 3, 4, 5, etc.).

Figure 2:
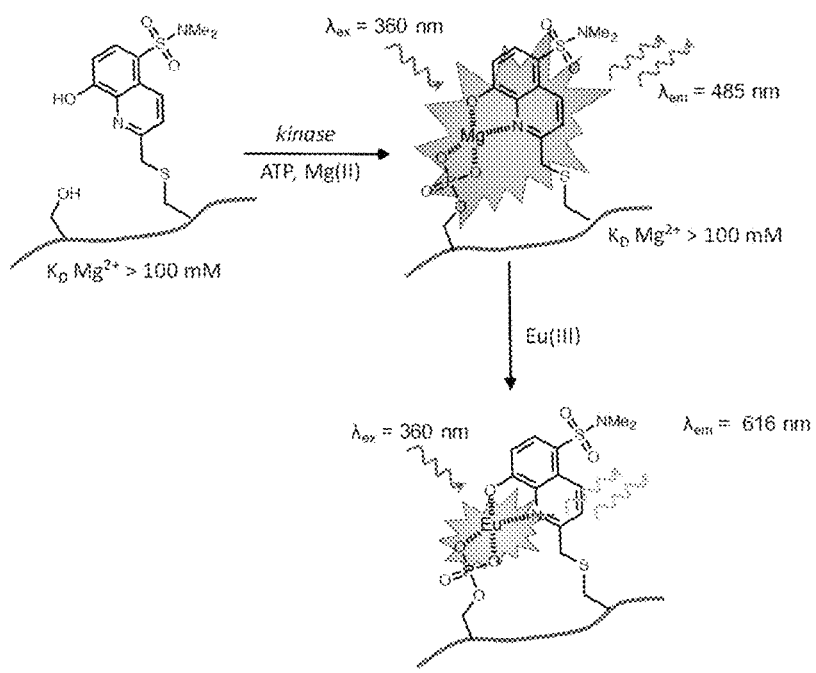
FIG. 2 illustrates the application of Eu(III), in another embodiment of the invention.

In some embodiments, the reporter group may be a side chain of an amino acid residue within the peptide or protein (i.e., R in the backbone structure . . . —NH—CHR—C(=O)— . . . ). (Thus, this may have a structure similar to glycine, in which alpha —CH is replaced by the reporter group.) In another set of embodiments, the reporter group may be attached to a side chain of an amino acid residue. For example, the reporter group may be covalently bonded to the sulfur of a cysteine residue within the peptide or protein, forming a disulfide linkage (e.g., upon reaction of a thiol within the reporter group to the thiol group within the cysteine) or a thioether linkage (e.g., upon reaction of a haloalkyl group within the reporter group to the thiol group within the cysteine), for instance, as is shown in the example of FIG. 2. As another non-limiting example, reaction of an amine within the reporter group to a carboxylic acid can be used to form an amide linkage, e.g., to amino acid residues such as aspartic acid or glutamic acid.

Accordingly, as a non-limiting example, the reporter group may have a structure:

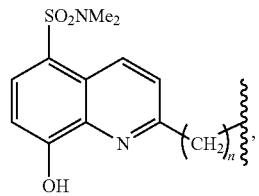

for example, where the —$(CH_2)_n$— group is bound to the sulfur of a cysteine residue, to a disulfide group (e.g., of a cysteine residue), to an amide linkage, to a backbone structure (e.g., as R in the backbone structure . . . —NH—CHR—C(=O)— . . . ), or the like. Other reporter groups that may be used in other embodiments include any of those described herein. The reporter group may be part of a common peptide or other common structure. A non-limiting example of such a peptide is LVEPLTPCGEA (SEQ ID NO: 1), discussed in more detail in Example 2.

Accordingly, as mentioned, a complex may be formed if the reporter group, a phosphate derivative, and a lanthanide ion are present. As a non-limiting example, if Eu(III) is present, then a complex such as the following may be formed (again, coordination to other ligands, such as $H_2O$, are not illustrated here for purposes of clarity):

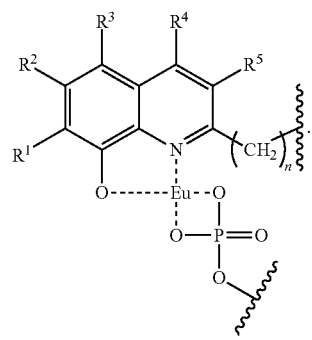

Eu(III) may, for example, may be 8 or 9 coordinate. Such a complex can accordingly be used to determine, for example, if a lanthanide ion such as Eu(III) is present, and/or to determine if a phosphorylation has occurred. As a non-limiting example, as certain amino acids can be phosphorylated upon reaction with a kinase (e.g., a protein kinase), the presence of this complex may be used to determine the presence and/or activity of kinases.

The concentrations of the peptide (or other structure) may be, for example, between about 0.1 micromolar to 10 mM. For example, the concentration may be at least 0.1 micromolar, at least 0.3 micromolar, at least 1 micromolar, at least 3 micromolar, at least 10 micromolar, at least 30 micromolar, at least 100 micromolar, at least 300 micromolar, at least 1 millimolar, at least 3 millimolar, and/or no more than 10 millimolar, no more than 3 millimolar, no more than 1 millimolar, no more than 300 micromolar, no more than 100 micromolar, no more than 30 micromolar, no more than 10 micromolar, no more than 3 micromolar, no more than 1 micromolar, or no more than 0.3 micromolar, including combinations of any of these ranges. Any suitable phosphoryl donor source may be used, e.g., adenosine 5'-triphosphate (ATP), for example, at concentrations between 1 micromolar and 10 millimolar. However, other concentrations can be used in other embodiments. Those of ordinary skill in the art will be able to prepare such peptides, e.g., using techniques such as standard (N-alpha)-Fmoc-amino acid protection chemistry together with standard solid-phase peptide synthesis.

In some cases, protection and selective deprotection of amino acids may be used, e.g., to modify a side chain or a residue. For example, orthogonal side-chain protection techniques may be used, such as the O-allyl ester (OAll) (e.g., for the carboxyl group in the side chain of glutamic acid or aspartic acid, for example), the allyloxy carbonyl (Alloc) (e.g., for the amino nitrogen in the side chain of lysine or ornithine, for example), p-methoxytrityl (MMT) or acetamidomethyl (Acm) (e.g., for the sulfhydryl of cysteine). As non-limiting examples, OAll and Alloc can be removed by Pd, Acm can be removed by iodine treatment, and MMT can be removed by mild acid treatment.

Examples of kinases include, but are not limited to, serine/threonine and tyrosine kinases. The concentration of the kinase can range from, as non-limiting examples, about 1 picomolar to about 1 micromolar. Exemplary kinases include cAMP dependent protein kinase, protein kinase C, Ca/calmodulin dependent kinases, AMP activated kinase, s6 kinases, eIF-2 kinases, p34cdc2 protein kinase, mitogen activated protein kinases, casein kinase-2, casein kinase-1, glycogen synthase kinase-3, Tyr-specific protein kinases. Other non-limiting examples of protein kinases include AGC kinases (e.g., PKA, PKC, PKG, etc.), CaM kinases (calcium/calmodulin-dependent protein kinases), CK1 kinases (casein kinase 1), CMGC kinases (e.g., CDK, MAPK, GSK3, CLK kinases), STE kinases (yeast Sterile kinases), TK kinases (tyrosine kinases), TKL kinase (tyrosine-kinase like kinases). Protein kinases also include serine/threonine-specific protein kinases (e.g., CK2, PKA, PKC, Mos/Raf kinases, MAPKs, CaM kinases, phosphorylase kinase, PKB, IRAK-1, etc.), tyrosine-specific protein kinases (e.g., PDGFR, EGFR, IGF1R, SCF, etc.). Still other examples of kinases include, but are not limited to, lipid kinases, carbohydrate kinases, nucleoside-phosphate kinases, and nucleoside-diphosphate kinases. In addition, it should be understood that the invention is not limited to only kinase detection. For instance, in certain embodiments, the state of phosphorylation of a peptide or other structure may be desired, i.e., not necessarily one that has been exposed to a kinase.

In addition, as previously discussed, certain embodiments of the present invention are generally directed to phosphatases, including tyrosine phosphatases, serine phosphatases, or the like. In some cases, the phosphatases are relatively promiscuous, and may recognize more than one substrate.

As mentioned, the complex, if present, can be determined by luminescence emission in accordance with certain aspects. In some cases, the complex may be determined, qualitatively or quantitatively, by determining light emitted by the complex when exposed to incident light of a suitable wavelength. Any method known to those of ordinary skill in the art can be used to determine luminescence, including, for example, fluorimeters, spectrofluorimeters, fluorescence plate readers, photomultiplier tubes, avalanche photodiodes, or the like.

In some cases, incident light of around 360 nm may be used to stimulate the complex. The incident light may have a wavelength of, for example, 360+/−20 nm, 360+/−10 nm, or 360+/−5 nm. In some cases, light of other frequencies (or frequency distributions) may be used.

In certain embodiments, europium ions or other lanthanide ions may be used due to their emission frequencies, and/or their lifetimes (i.e., after excitation). For example, in certain cases, europium ions may exhibit emission wavelengths of around 615 nm to 620 nm and around 580 nm to 600 nm. For instance, the emission may be monitored around 616 nm, e.g., 616+/−20 nm, 616+/−10 nm, or 616+/−5 nm or at other relevant Eu(III) luminescence emission bands. Such wavelengths may allow for surprisingly little background interference, e.g., from other organic or biological species.

In addition, chelated europium ion complexes may exhibit lifetimes on the order of microseconds to milliseconds, in contrast to non-lanthanide ions and organic fluorophore that may exhibit lifetimes on the order of nanoseconds. The longer lifetimes may thereby allow for easier detection. For example, in some instances, the longer lifetimes can allow emissions from interfering background organic or biological species to be "gated" out, for example, by using a short time delay before determining the lanthanide ion luminescence. Accordingly, complexes comprising europium ions (or other lanthanide ions) may be easier to detect in certain embodiments than other, non-lanthanide ion chelates.

In some aspects, the europium ion (or other lanthanide ion) may directly bind non-covalently to or chelate with the reporter group and the phosphate group, e.g., to form structures such as those shown herein. For example, a solution may contain a peptide (or other structure as discussed herein) suspected of being phosphorylated (e.g., upon exposure to a kinase). The peptide may also contain a reporter group. The solution may also contain europium ions and/or other lanthanide ions, e.g., which can be added when the solution is formed, or afterwards. For example, such ions may be added before or after exposure of a peptide or other structure to a kinase, or a phosphatase. In some cases, binding of europium ions to form a complex may occur spontaneously, e.g., under ambient temperatures and/or pressures.

In some embodiments, a complex may initially be formed using other ions, which ions may then be exchanged or replaced with europium ions or other lanthanide ions. For instance, in some cases, an ion such as magnesium may first complex to the reporter group and the phosphate group, and the ion may then be exchanged or replaced with europium ions or other lanthanide ions. A non-limiting example of such a reaction is shown in FIG. 2. The other ion and the lanthanide ion may both be present initially, or in some cases, the lanthanide ion may be added after formation of the complex. The ion exchange within the complex may be partial or total, i.e., 100% or a smaller percentage of the ions within the complex may be replaced by europium or other lanthanide ions, depending on factors such as ion concentration, temperature, duration, or the like.

The methods as discussed herein can be used in vitro or in vivo. In some applications, a reaction may be conducted in a buffer containing suitable ions, phosphates, and/or kinases, phosphatases, etc., depending on the application. Suitable buffers include, but are not limited to, HEPES, MES, TRIS, or the like.

In some cases, the reaction may occur inside a cell. The cell may include sufficient kinases, phosphatases, $Mg^{2+}$, ATP sources, etc., e.g., in the cytosol. In some cases, additional ions, such as europium or other lanthanides may also be added. In certain embodiments, cellular internalization sequences can be used. Non-limiting examples of cellular internalization sequences include penetratins, HIV-TAT domains and poly-arginine sequences. However, it should be understood that cells are not required, and in some embodiments, reactions such as those discussed herein may occur in vitro.

In addition, in some embodiments, the hydroxyquinoline-modified phosphopeptides as their europium ion chelates or other phosphopeptide-lanthanide ion complexes can be used as phosphatase substrates. In some cases, phosphatase activity will remove the phosphate and as a result, luminescence will decrease due to reduced affinity for the lanthanide; thus, some or all of the hydroxyquinoline-modified peptides that serve as kinase substrates can similarly serve as phosphatase substrates once phosphorylated in certain embodiments.

In any of the amino acid sequences described herein, it should be understood that the sequence can have any suitable C-terminus, for example, one that is capped with an amide (e.g., a primary amide), or is not capped; and independently, the sequence can have any suitable N-terminus, for example, one that is free, or is N-acetylated.

U.S. Pat. Nos. 7,262,282 and 7,964,729 are incorporated herein by reference in their entireties.

In addition, U.S. Provisional Patent Application Ser. No. 62/641,587, filed Mar. 12, 2018, entitled "Kinase and/or Phosphatase Sensing Via Hydroxyquinoline-Sensitized Chelates," by Imperiali, et al., is incorporated herein by reference in its entirety.

The following examples are intended to illustrate certain embodiments of the present invention, but do not exemplify the full scope of the invention.

Example 1

This example illustrates selective protein kinase activity assays using a fluorescent readout at 485 nm due to the formation of an Mg(II)-bound CSox-phospho-peptide chelate. See also FIG. 2.

The same peptides can also be applied in a quenched point readout, e.g., at the end of a kinetic analysis where the assay mixture is added to a buffer containing Eu(III) ions, regardless of whether the enzyme reaction has been stopped or not. The Eu(III) displaces the Mg(II) and forms a new chelate that shows sensitized emission with a maximum luminescence around 616 nm. This is at a wavelength where there may be little or no background interference. Due to the relatively long lifetime of the Eu(III) chelate, any emission from any interfering background fluorescent organic species may also be "gated" out in certain embodiments by applying a short delay (e.g., 10 to 500 microseconds or longer) before collecting the Eu(III) luminescence data.

Example 2

This example illustrates Sox-Eu peptide sensors to probe kinase activity, in accordance with certain embodiments of the invention.

FIG. 2 shows schematic representations of a Eu(III)-based Sox sensor to probe protein kinase activity in this example. The Sox-containing substrate is silent, but upon phosphorylation, the chromophore can bind Eu(III) and undergo chelation-enhanced luminescence.

The instrumentation used in this example is as follows. The UV-Vis spectrophotometer was a NanoDrop ND-1000 (Labtech). The fluorimeter was a CLARIOstar® spectrofluorimeter equipped for time-resolved fluorescence measurements (BMG LABTECH). The plate was a Greiner assay plate (Greiner Bio-One), 96-well, no lid, flat bottom, medium binding surface, non-sterile, black polystyrene.

For the stock solutions, only reagents of the highest purity and lowest metal ion content were used. Stock solutions of the peptides were prepared in doubly deionized water and concentrations were determined by UV-Vis (based on the determined extinction coefficient of the fluorophore unit, 5-(N,N-dimethylsulfonamido)-8-hydroxy-2-methylquinoline, $\varepsilon_{355}$ (epsilon)=8247 $M^{-1}$ $cm^{-1}$ at 355 nm in 0.1 M NaOH with 1 mM $Na_2EDTA$). An average of the values from three separate solutions, each prepared using a different volume of the stock solution, was read on the UV-Vis spectrophotometer. Purified peptide stock solutions could be stored at 4° C. for at least 6 months or −20° C. for longer periods.

A europium chloride ($EuCl_3$) stock solution of 50 mM (99.99% trace metals basis, Aldrich) was prepared in ultrapure water. 500 mM HEPES (SigmaUltra) was prepared and adjusted to pH 7.5 with NaOH (99.998+%, Aldrich) solution. 5 M NaCl was prepared by dissolving sodium chloride (SigmaUltra) in ultrapure water.

The luminescence experiments were conducted as follows. Time-resolved emission measurements were made with a CLARIOstar® spectrofluorimeter. The spectra were recorded between 410 and 700 nm, and all measurements were made using the following settings: excitation wavelength 360 nm; delay time 0.4 ms; stepwidth 1.0 nm; emission bandwidth 8 nm; gain: 3000; focal height 8 nm; 20 flashes per well. All of the spectra were corrected for background luminescence by subtracting a blank scan of the solvent solution.

Comparison of phosphopeptide (Sox-P) and unphosphorylated biosensor (Sox-OH). Time-resolved luminescence spectra of the phosphopeptide Sox-P (5 micromolar) and the corresponding unphosphorylated biosensor Sox-OH (5 micromolar) at 30° C., in 50 mM HEPES buffer, pH 7.5, 100 mM NaCl, were recorded in the fluorometer. The difference in luminescence was determined by comparing the luminescence intensity at the maximum emission wavelength (620 nm) of synthetic phosphopeptide and unphosphorylated peptide. The reported values are averages of three separate experiments.

Figure 3:
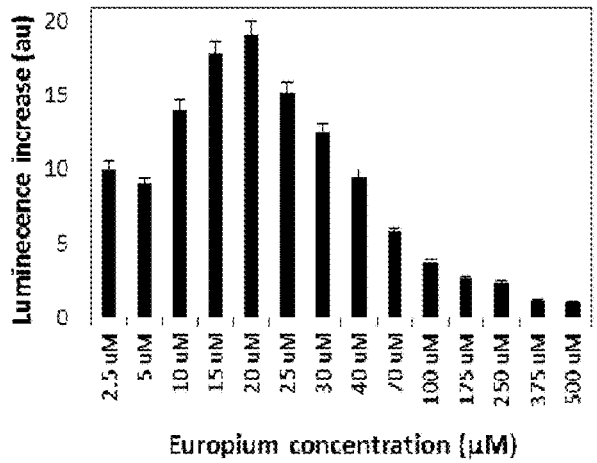
FIG. 3 illustrates the luminescence changes between a peptide and a phosphopeptide in the presence of increasing Eu(III) concentrations, in yet another embodiment of the invention.
Figure 4:
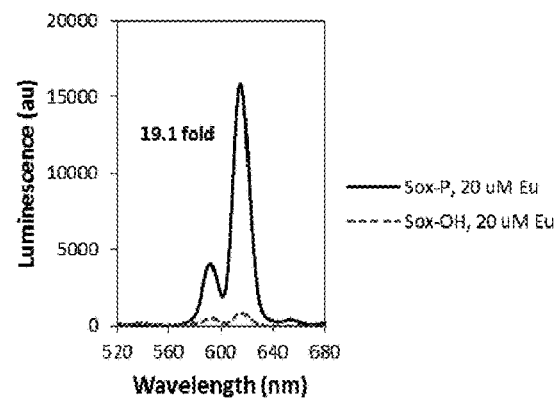
FIG. 4 shows a spectral comparison of a phosphorylated and an unphosphorylated peptide in the presence of a single concentration of Eu(III), in still another embodiment of the invention.

FIG. 3 shows luminescence difference between the phosphorylated peptide (Sox-P) and the corresponding substrate (Sox-OH) using different concentrations of $EuCl_3$. FIG. 4 shows a comparison of the spectra of phosphorylated (Sox-P, 5 micromolar) and the unphosphorylated peptide (Sox-OH, 5 micromolar) in the presence 20 micromolar of $EuCl_3$.

Determination of Eu(III) dissociation constants ($K_D$). Eu(III) titrations were performed at 30° C. in a buffer containing 50 mM HEPES buffer, pH 7.5, 100 mM NaCl, and 5 micromolar of the of the phosphopeptide Sox-P (5 micromolar) or the corresponding unphosphorylated biosensor Sox-OH (5 micromolar) in a total volume of 200 microliters. Aliquots of $EuCl_3$ stock solutions were added (for the final $EuCl_3$ concentration in the well to be in the range of approximately 2.5-6000 micromolar) and the data was recorded in the fluorometer. Data were fit with the program GraFit 7. The reported values are averages of three separate experiments.

Figure 5:
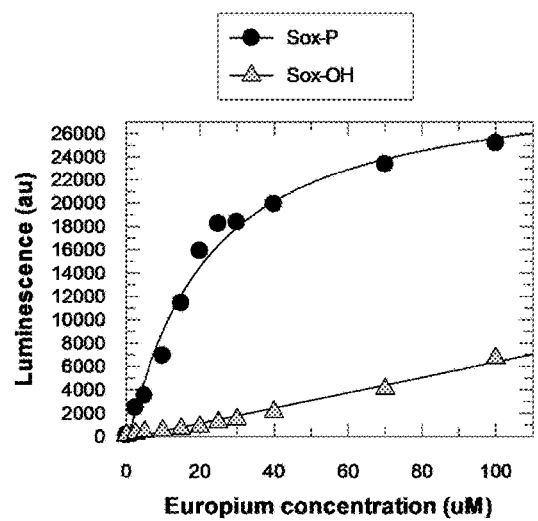
FIG. 5 illustrates Eu(III) titration curves for another peptide and a phosphopeptide, in another embodiment of the invention.

FIG. 5 shows Eu(III) titration curves for Sox-OH and Sox-P. Table 1 shows peptide Sequences and Dissociation Constants for Eu(III).

TABLE 1

| Entry | Peptide | Peptide Sequence | Eu(III) $K_D$ (micromolar) |
|---|---|---|---|
| 1 | Sox-OH | LVEPLTPC(Sox)GEA (SEQ ID NO: 2) | 1570.3 +/- 476.0 |
| 2 | Sox-P | LVEPLT*PC(Sox)GEA (SEQ ID NO: 3) | 18.4 +/- 4.0 |

Example 3

This example shows an illustration of binding using a CSox substrate for detecting the activity of certain tyrosine kinases. The instrumentation used in this example was a Biotek Synergy Neo2 microplate reader. In this reaction, depicted in FIG. 2, a 100 microsecond delay allows binding of Eu(III) to be determined within the complex as shown. Time-resolved fluorescence at >600 nm emission allows for the elimination of compound interference. In particular, in this example, a kinase activity was determined by fluorescence using CSox peptide Ac-EEPIYVC(Sox)FG (SEQ ID NO: 4), in combination with europium ions.

The reaction conditions used included 50 mM HEPES (pH 7.5), 5-1000 micromolar ATP, 1 mM DTT, 0.01% Brij-35, 1% glycerol, 0.2 mg/ml BSA, 2-20 mM $MgCl_2$, 10 micromolar CSox peptide, 1-5 nM YES (a kinase), amino acids 1-543 (Carna Bio).

The reaction was set up using 10 microliters CSox-peptide (5×), 30 microliters reaction mix with ATP & DTT (1.67×), 5 minute preincubation (all components except EDB/YES) at 30° C., 10 microliters enzyme dilution buffer (lx) or YES (5× in EDB) to 1% glycerol final in a 50 microliter final reaction volume.

Reads were performed kinetically with an excitation wavelength of 360 nm and an emission wavelength of 485 nm (filter, 20 or 40 nm bandwidth), and measuring fluorescence intensity from the top of the plate. For the endpoint assay, following addition of europium ion (50 to 1,000 micromolar), the fluorescence signal was determined using an excitation wavelength of 360 nm and an emission wavelength of 620 nm (filter, gain=100) or as wavelength scan from 500 to 680 nm, using time resolved-fluorescence (0.1 msec delay) and a gain of 200.

The enzyme dilution buffer (EDB) was 20 mM HEPES, pH 7.5, 0.01% Brij-35, 5% glycerol, 1 mM DTT, and 1 mg/mL Bovine Serum Albumin (BSA). Thus, the actual final reaction concentrations were 54 mM HEPES, pH 7.5, 0.012% Brij-35, 1% glycerol, 1.2 mM DTT, and 0.2 mg/mL BSA. All components except the enzyme were equilibrated to 30° C. The reactions were run in Corning, half-area 96-well, white flat round bottom polystyrene NBS microplates after sealing using optically-clear adhesive film (TopSealA-Plus plate seal, PerkinElmer, applied with a roller) to eliminate evaporation and resulting drift.

Figure 6A:
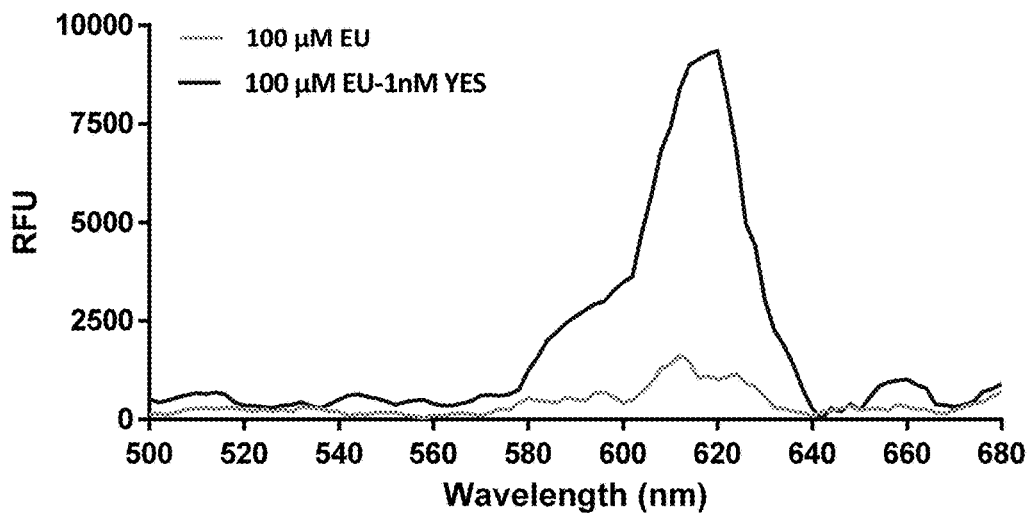
FIGS. 6A-6C illustrate Eu binding using a CSox substrate, in accordance with yet another embodiment of the invention.
Figure 6B:
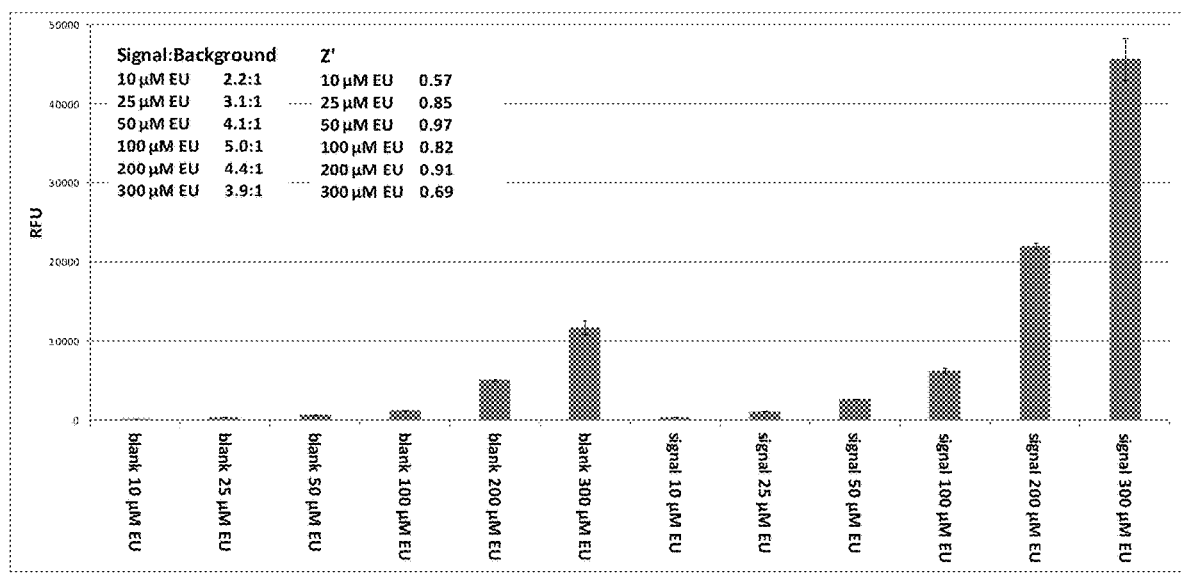
Figure 6C:
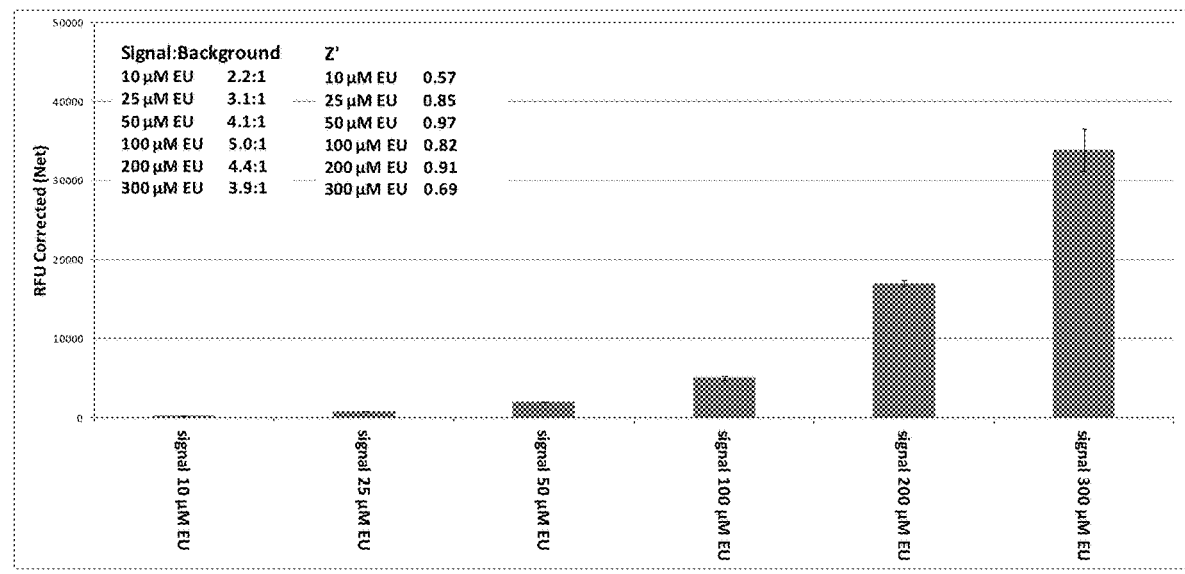

FIGS. 6A-6C show results for Eu(III) titration using 50-300 micromolar using 1 nM YES & CSox substrate Ac-EEPIYVC(Sox)FG (SEQ ID NO: 4). The reaction was run for 30 minutes with 1 nM YES, 10 micromolar CSox substrate, 5 mM $MgCl_2$, 100 micromolar ATP, and 10-300 micromolar europium. Signals in the presence of Eu(III) were much greater than blanks or controls, with generally greater signals at higher concentrations. Z' values were greater than 0.5, considered to be an excellent assay, throughout the range tested.

Example 4

Figure 7A:
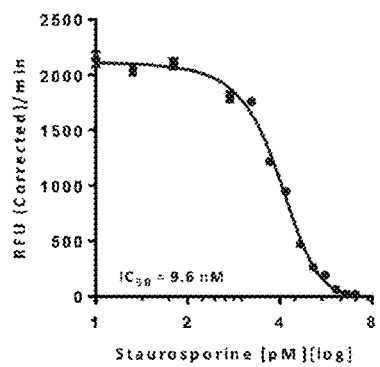
FIGS. 7A-7C illustrate the application of a hydroxyquinoline-sensitized Eu chelate to determine the $IC_{50}$ of staurosporine using a YES kinase, in one embodiment of the invention.
Figure 7B:
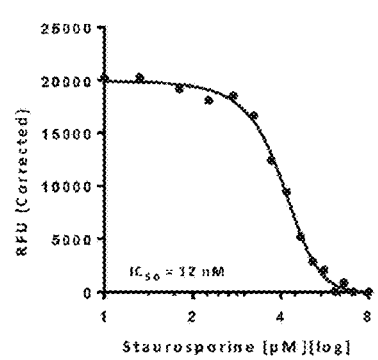
Figure 7C:
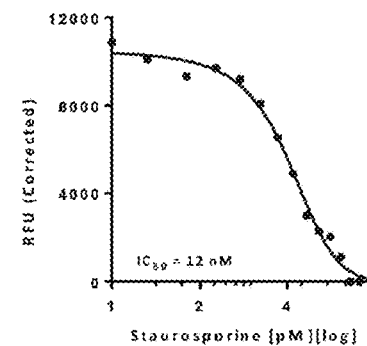

This example shows the application of a hydroxyquinoline-sensitized Eu chelate with an acetyl and primary amide-capped tridecapeptide with a Thr-Val-CSox-Ala-Leu (SEQ ID NO: 5) core to determine the $IC_{50}$ of staurosporine using a YES kinase. A comparison kinetic vs endpoint (Eu) assay is shown in FIGS. 7A-7C. The reaction was performed for 30 minutes with 1 nM YES, 10 micromolar AQT0104, 15 mM $MgCl_2$, 200 micromolar ATP, and then 200 micromolar of Eu was added. These results were consistent with the values reported for YES using a PE/caliper MBS Assay.

Example 5

This example illustrates the application of a hydroxyquinoline-sensitized Eu chelate with an acetyl and primary amide-capped tridecapeptide with a Tyr-Arg-CSox-Pro-Ser (SEQ ID NO: 6) core to determine the $IC_{50}$ of staurosporine $IC_{50}$ using a CaMK2δ kinase. A comparison kinetic vs endpoint (Eu) assay is shown in FIGS. 8A-8B. In both figures, the concentrations were as follows: CaMK2δ kinase, 1 nM; ATP, 5 micromolar; and peptide, 10 micromolar.

Example 6

This example illustrates the application of a hydroxyquinoline-sensitized Eu chelate with an acetyl and primary amide-capped hexadecapeptide with an Ac-CSox-Gly-Thr-Phe (SEQ ID NO: 7) core to assess activity of ASK1 kinase at low and high ATP concentrations. The results are shown in FIGS. 10A and 10B. High S/B (signal to background) (4.5 or higher) and Z' (0.6 for low ATP and 0.86 for high ATP conditions) were observed.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of."

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

When the word "about" is used herein in reference to a number, it should be understood that still another embodiment of the invention includes that number not modified by the presence of the word "about."

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A composition, comprising:
a peptide having a first portion comprising a structure:

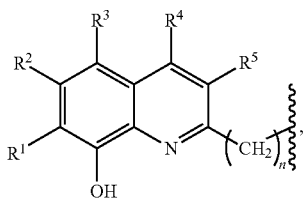

wherein each of $R^1$, $R^2$, $R^3$, $R^4$, and $R^5$ independently is hydrogen or —$SO_2X$ such that at least one of $R^1$, $R^2$, $R^3$, $R^4$, and $R^5$ is —$SO_2X$, wherein X is —OR' or —NR'R", R' and R" each independently being hydrogen or an alkyl group, and n is 0 or a positive integer, and
a second portion comprising a phosphate group,
wherein the N and/or the O of the first portion, and the phosphate group of the second portion, are coordinated via an europium ion in the 3+ state (Eu(III)).

2. The composition of claim 1, wherein the peptide comprises a structure:

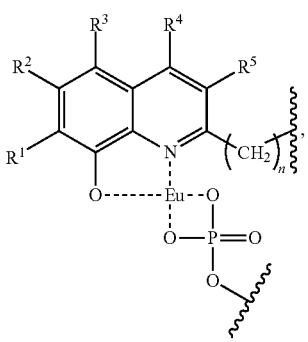

wherein:
Eu is the europium ion; and
the wavy lines indicate covalent binding of the structure to the peptide.

3. The composition of claim 2, wherein Eu is further coordinated to a plurality of $H_2O$ molecules.

4. The composition of claim 1, wherein $R^1$ is —H and/or $R^2$ is —H and/or $R^4$ is —H and/or $R^5$ is —H.

5. The composition of claim 1, wherein the structure has only one —$SO_2X$.

6. The composition of claim 1, wherein $R^3$ is —$SO_2X$.

7. The composition of claim 6, wherein X is —NR'R".

8. The composition of claim 7, wherein R' and R" are each an alkyl group.

9. The composition of claim 1, wherein the phosphate group is a portion of a phosphorylated amino acid residue within the peptide.

10. The composition of claim 9, wherein the phosphorylated amino acid is serine or threonine or tyrosine.

11. The composition of claim 1, wherein n is 0, 1, or 2.

12. The composition of claim 1, wherein the —$(CH_2)_n$— of the structure is covalently bound to a second amino acid residue within the peptide.

13. The composition of claim 12, wherein the second amino acid residue is cysteine.

14. The composition of claim 13, wherein the —$(CH_2)_n$— of the structure is covalently bound to the sulfur atom of the cysteine residue.

15. The composition of claim 12, wherein the —$(CH_2)_n$— of the structure is covalently bound to an amino acid backbone of the peptide.

16. The composition of claim 15, wherein the phosphorylated amino acid and the second amino acid residue are separated by at least one amino acid residue.

17. The composition of claim 15, wherein the phosphorylated amino acid and the second amino acid residue are separated by 1-5 amino acid residues.

18. A method, comprising:
noncovalently binding an Eu(III) ion to a peptide comprising a first portion, and a second portion comprising a phosphate group, the first portion having a structure:

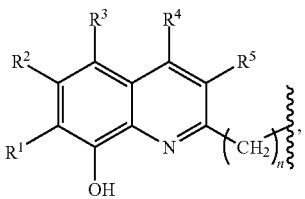

wherein:
each of $R^1$, $R^2$, $R^3$, $R^4$, and $R^5$ independently is hydrogen or —$SO_2X$ such that at least one of $R^1$, $R^2$, $R^3$, $R^4$, and $R^5$ is —$SO_2X$, wherein X is —OR' or —NR'R", R' and R" each independently being hydrogen or an alkyl group, n is 0 or a positive integer, and the wavy line indicates covalent attachment to the peptide; and determining luminescence of the structure to determine binding of the Eu(III) ion to the first and second portions of the peptide.

19. The method of claim 18, wherein the peptide is prepared by exposing a precursor peptide having a phosphorylatable amino acid residue to a kinase able to phosphorylate the phosphorylatable amino acid residue to produce the phosphopeptide.

20. A composition, comprising:
a solution comprising dissolved Eu(III) ions and a peptide comprising a portion having a structure:

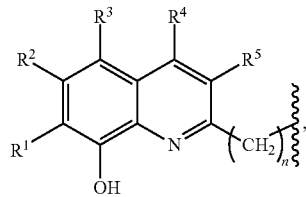

wherein:
each of $R^1$, $R^2$, $R^3$, $R^4$, and $R^5$ independently is hydrogen or —$SO_2X$ such that at least one of $R^1$, $R^2$, $R^3$, $R^4$, and $R^5$ is —$SO_2X$, wherein X is —OR' or —NR'R", R' and R" each independently being hydrogen or an alkyl group, n is 0 or a positive integer, and the wavy line indicates covalent attachment to the peptide.

21. The method of claim 18, wherein the phosphopeptide is exposed to a phosphopeptide phosphatase to produce the peptide.

* * * * *

UNITED STATES PATENT AND TRADEMARK OFFICE
CERTIFICATE OF CORRECTION

PATENT NO. : 10,799,603 B2  
APPLICATION NO. : 16/299976  
DATED : October 13, 2020  
INVENTOR(S) : Barbara Imperiali et al.

Page 1 of 1

It is certified that error appears in the above-identified patent and that said Letters Patent is hereby corrected as shown below:

On the Title Page

Item (71) Applicants:
"Massachusetts Institute of Technology, Cambridge, MA (US); Centre National de la recherche scientifique, Paris (FR); ENSCM, Montpellier (FR); UNIVERSITE DE MONTPELLIER, Montpellier (FR)"

Should read:
-- Massachusetts Institute of Technology, Cambridge, MA (US); Centre national de la recherche scientifique, Paris (FR); ENSCM, Montpellier (FR); UNIVERSITE DE MONTPELLIER, Montpellier (FR) --

Item (73) Assignees:
"Massachusetts Institute of Technology, Cambridge, MA (US); Centre National de la Recherche Scientifique, Paris (FR); ENSCM, Montpellier (FR); UNIVERSITE DE MONTPELLIER, Montpellier (FR)"

Should read:
-- Massachusetts Institute of Technology, Cambridge, MA (US); Centre national de la recherche scientifique, Paris (FR); ENSCM, Montpellier (FR); UNIVERSITE DE MONTPELLIER, Montpellier (FR) --

Signed and Sealed this  
Twentieth Day of April, 2021

Drew Hirshfeld  
*Performing the Functions and Duties of the*  
*Under Secretary of Commerce for Intellectual Property and*  
*Director of the United States Patent and Trademark Office*

SEQUENCE LISTING

```
<160> NUMBER OF SEQ ID NOS: 7

<210> SEQ ID NO 1
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 1

Leu Val Glu Pro Leu Thr Pro Cys Gly Glu Ala
1               5                   10

<210> SEQ ID NO 2
<211> LENGTH: 11
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (8)..(8)
<223> OTHER INFORMATION: may be modified by the structure on page 5
```

```
<400> SEQUENCE: 2

Leu Val Glu Pro Leu Thr Pro Cys Gly Glu Ala
1               5                   10

<210> SEQ ID NO 3
<211> LENGTH: 11
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (6)..(6)
<223> OTHER INFORMATION: PHOSPHORYLATED
<220> FEATURE:
<221> NAME/KEY: misc_feature
<222> LOCATION: (8)..(8)
<223> OTHER INFORMATION: may be modified by the structure on page 6

<400> SEQUENCE: 3

Leu Val Glu Pro Leu Thr Pro Cys Gly Glu Ala
1               5                   10

<210> SEQ ID NO 4
<211> LENGTH: 9
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (1)..(1)
<223> OTHER INFORMATION: may be modified by an acetyl group
<220> FEATURE:
<221> NAME/KEY: misc_feature
<222> LOCATION: (7)..(7)
<223> OTHER INFORMATION: may be modified by the structure on page 6

<400> SEQUENCE: 4

Glu Glu Pro Ile Tyr Val Cys Phe Gly
1               5

<210> SEQ ID NO 5
<211> LENGTH: 5
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: may be modified by the structure on page 6

<400> SEQUENCE: 5

Thr Val Cys Ala Leu
1               5

<210> SEQ ID NO 6
<211> LENGTH: 5
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: may be modified by the structure on page 6

<400> SEQUENCE: 6
```

```
Tyr Arg Cys Pro Ser
1               5

<210> SEQ ID NO 7
<211> LENGTH: 4
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (1)..(1)
<223> OTHER INFORMATION: may be modified by the structure on page 7
<220> FEATURE:
<221> NAME/KEY: misc_feature
<222> LOCATION: (1)..(1)
<223> OTHER INFORMATION: may be modified by an acetyl group

<400> SEQUENCE: 7

Cys Gly Thr Phe
1
```